United States Patent
Bardsley et al.

(10) Patent No.: US 6,677,326 B2
(45) Date of Patent: *Jan. 13, 2004

(54) CORTICOSTEROID FORMULATION COMPRISING LESS THAN 2.5 MG PREDNISOLONE FOR ONCE DAILY ADMINISTRATION

(75) Inventors: Hazel Judith Bardsley, Cambridge (GB); Robin Mark Bannister, Essex (GB); Julian Clive Gilbert, Essex (GB)

(73) Assignee: Arakis, Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/263,044

(22) Filed: Oct. 1, 2002

(65) Prior Publication Data

US 2003/0149009 A1 Aug. 7, 2003

Related U.S. Application Data

(63) Continuation of application No. PCT/GB01/04181, filed on Sep. 19, 2001, and a continuation-in-part of application No. 09/936,586, filed on Sep. 13, 2001, now Pat. No. 6,488,960.

(30) Foreign Application Priority Data

Mar. 15, 1999 (GB) .............................. 9905898
Sep. 21, 2000 (GB) .............................. 0023220

(51) Int. Cl.$^7$ .............................................. A61K 31/56
(52) U.S. Cl. ..................... 514/179; 514/180
(58) Field of Search ................................. 514/179, 180

(56) References Cited

U.S. PATENT DOCUMENTS 5,792,476 A    8/1998    Hällgren

FOREIGN PATENT DOCUMENTS

WO    WO 95/08323 A1    3/1995

OTHER PUBLICATIONS

Rote Liste, 1998, 31 037 Decortin H 1mg.
Buckley, L.M. et al., "Effects of Low Dose Corticosteroids on the Bone Mineral Density of Patients with Rheumatoid Arthritis" *The Journal of Rheumatology*, 1995, pp. 1055–1059, vol. 22, No. 6.
Cash, J.M. et al. "Pituitary–Adrenal Axis Responsiveness to Ovine Corticotropin Releasing Hormone in Patients with Rheumatoid Arthritis Treated with Low Dose Prednisone" *The Journal of Rheumatology*, 1992, pp. 1692–1696, vol. 19, No. 11.

*Primary Examiner*—James H. Reamer
(74) *Attorney, Agent, or Firm*—Saliwanchik, Lloyd & Saliwanchik

(57) ABSTRACT

The subject invention concerns a unit dose formulation comprising less than 2.5 mg of prednisolone or an equivalent, equipotent amount of another corticosteroid. One embodiment of a method of the invention concerns once daily administration of the unit dose formulation between midnight and 6 a.m. for the treatment of rheumatoid arthritis.

17 Claims, 1 Drawing Sheet

Figure 1:
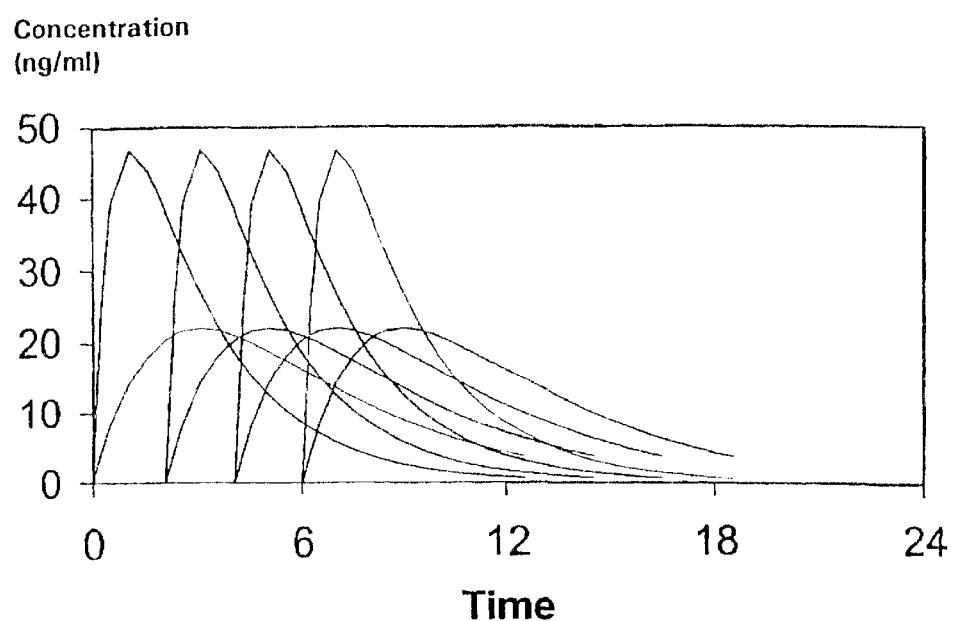

CORTICOSTEROID FORMULATION COMPRISING LESS THAN 2.5 MG PREDNISOLONE FOR ONCE DAILY ADMINISTRATION

CROSS-REFERENCE TO RELATED APPLICATIONS

This application is a continuation of International Application PCT/GB01/04181, with an international filing date of Sep. 19, 2001, published in English under PCT Article 21(2), and is a continuation-in-part of U.S. application Ser. No. 09/936,586, filed Sep. 13, 2001 now U.S. Pat. No. 6,488,960.

FIELD OF THE INVENTION

This invention relates to a controlled-release formulation, and in particular to a formulation of a corticosteroid, suitable for use in the treatment of rheumatoid arthritis.

BACKGROUND OF THE INVENTION

Glucocorticoids, and in particular prednisone and prednisolone, are widely used for the treatment of rheumatoid arthritis. The use of glucocorticoids may be efficacious but has disadvantages, particularly in terms of side-effects such as bone loss.

It appears to be generally recognized that it would be desirable to use low doses of, say, prednisolone, in the treatment of rheumatoid arthritis. While it is clear that low dose oral prednisolone can be efficacious, there is some controversy over what is actually meant by a low dose.

Kirwan, New England J. Med. 333:142–5 (1995), indicates that a daily dosage of 7.5 mg prednisolone is effective. This is supported by Boers et al., The Lancet 350:309–318 (1997). Boers et al. also reports that a typical treatment of rheumatoid arthritis following initial treatment with a non-steroidal anti-inflammatory drug (NSAID) involves a high initial dose and, when the condition is under control, reduced doses, down to a "low maintenance" of 7.5 mg/day.

Gotzsche and Johansen, B. M. J. 316:811–818 (1998), reviews a number of studies of low dose prednisolone in the treatment of rheumatoid arthritis. Most of these studies report doses of at least 7.5 mg. There is one report, but from as long ago as 1967, of a 2.5 mg dose.

It is evident that, in clinical practice, rheumatologists taper the dose of glucocorticoid to as a low a level as they can, before symptoms return. There may be patients who are stable on less than 5 mg prednisolone per day, but there is little or no clinical data to support that such a low dose is actually providing any benefit. This is important, because in many of these patients, prednisolone may be contributing only side-effects. There is no evidence that any dose of prednisolone, lower than those generally used, is effective when given chronically for the treatment of rheumatoid arthritis.

Arvidson et al., Annals of the Rheumatic Diseases 56:27–31 (1997), reports that the timing of glucocorticoid administration in rheumatoid arthritis may be important, in controlling the acute inflammatory aspects of the disease. In the reported study, patients were woken at 2.00 a.m. and given 7.5 mg or 5 mg prednisolone.

U.S. Pat. No. 5,792,496 claims a sustained-release formulation of a glucocorticoid such as prednisone or prednisolone. The formulation comprises 2.5–7 mg of the glucocorticoid and releases at least 90% of the drug during 40–80 minutes, starting about 1–3 hours after the entry of the drug into the small intestine. The intention is that the formulation should be taken immediately before the patient goes to sleep, that the drug should be released during sleep, and that the greatest secretion of cytokines (which occur shortly before waking) should thus be treated most effectively. This is based on the same data as in Arvidson et al., supra, i.e. using doses of 5 or 7.5 mg prednisolone given at 2 a.m.

BRIEF SUMMARY OF THE INVENTION

This invention is based on the discovery that, in a study designed to test the reproducibility of the results reported by Arvidson et al. (and in U.S. Pat. No. 5,792,496), a much lower dosage of the glucocorticoid was also effective. Given the state of the art and the known side-effects of corticosteroids, this increase in their therapeutic index is surprising.

According to the present invention, a unit dosage comprises less than 2.5 mg of prednisolone or an equivalent amount of a corticosteroid. Equivalence is in terms of potency. It will be understood that drugs vary in potency, and that doses can therefore vary, in order to obtain equivalent effects.

Thus, in accordance with the present invention, a controlled-dose formulation of the drug is adapted to release the drug at a predetermined period of time after administration, or at a predetermined time. Advantages of the invention may include enhanced efficacy, reduced side-effects and/or reduced $C_{max}$. Further or in addition, chronotherapeutic administration allows the use of a reduced level of active material.

DESCRIPTION OF THE INVENTION

The intention behind the invention is that the active ingredient should be released at a predetermined time, e.g. between midnight and 6 a.m., e.g. 2 a.m. and 4 a.m., or a predetermined time after administration. Thus, the user can take the formulation before going to sleep, but have the full value of an effective dosage of the drug during the night, or during sleep, at a dosage that has minimal side-effects. Accordingly, a predominant amount of the active ingredient, e.g. at least 90% by weight, is released at least 2 or 3 hours after administration, and preferably no more than 6, 7 or 8 hours after administration.

Formulations of the invention are intended for the treatment of disorders associated with the release of cytokines, e.g. TNF α, IL-1, IL-2, IL-6 and IL-8. In particular, the invention is suitable for the treatment of inflammatory diseases, including polyarthropathies, and more especially rheumatoid arthritis, asthma, inflammatory bowel disease, chronic obstructive pulmonary disease, psoriasis, psoriatic arthritis, polymyalgia rheumatica and atopic dermatitis. The drug that is used in the formulation may be chosen accordingly. If desired, the active ingredient may be formulated as a pro-drug, so that the active component is released in vivo.

Among active agents that can be used in the invention, examples are glucocorticoids and other corticosteroids, e.g. budesonide, methylprednisolone, deflazacort, fluticasone, prednisone and prednisolone. The appropriate dosage of each such drug depends on its potency.

Equivalent potency in clinical dosing is well known. Information relating to equivalent steroid dosing (in a non-chronotherapeutic manner) may be found in the British National Formulary (BNF), 37 March 1999, the content of which is incorporated herein by reference.

The BNF guidelines are included in the table below. In addition, the proposed clinical dose equivalent to 1 mg of prednisolone when administered in a chronotherapeutic manner is included in the table. More specifically, the following Table is of doses of steroids equivalent to mg of prednisolone and equivalence to 1 mg of prednisolone when administered in a chronotherapeutic manner according to this invention and 1 mg of prednisolone.

| Steroid | Equivalent dose in chronotherapeutic administration | |
| --- | --- | --- |
| | Equal to 5 mg prednisolone (Normal dosing)* | Equal to 1 mg prednisolone |
| betamethasone | 750 μg | 150 μg |
| cortisone acetate | 25 mg | 5 mg |
| deflazacort | 6 mg | 1.2 mg |
| dexamethasone | 750 μg | 150 μg |
| hydrocortisone | 20 mg | 4 mg |
| methyl prednisone | 4 mg | 0.8 mg |
| prednisone | 5 mg | 1 mg |
| triamcinolone | 4 mg | 0.8 mg |

It is also known (BNF 37 March 1999) from clinical dosing equivalence that doses of triamcinolone, fluticasone and budesonide are broadly similar in nasal administration (110 μg, 100 μg and 200 μg). A chronotherapeutic advantage may be expected upon dosing these drugs.

Corticosteroids such as cortisone acetate and hydrocortisone are less preferred for use in the invention, owing to their systemic side-effects on long-term use. Such compounds, having effect on glucose and mineral metabolism, will be known to those skilled in the art.

The preferred route of administration of a formulation of this invention is oral. However, it will be readily apparent to those skilled in the art that other routes of administration may be used, e.g. having regard to the nature of the condition being treated and the most effective means of achieving delayed release.

The drug may be administered in any conventional formulation that provides delayed release, via any suitable route of administration. Conventional dosing parameters may be adopted, i.e. those which are known to or adapted to the practice of those skilled in the art. The daily dosage (relative to prednisolone) is usually at least 0.25 or 0.5 mg, e.g. 1 to 2 mg, but will be chosen according to the age, weight and health of the subject, and other factors that are routinely considered by the man skilled in the art.

A formulation of the invention may be a unit dosage such as a tablet, capsule, ampoule, vial or suspension. A controlled-release formulation may be in matrix, coating, reservoir, osmotic, ion-exchange or density exchange form. It may comprise a soluble polymer coating which is dissolved or eroded, after administration. Alternatively, there may be an insoluble coating, e.g. of a polymer, through which the active ingredient permeates, as from a reservoir, diffuses, e.g. through a porous matrix, or undergoes osmotic exchange. A further option for a controlled-release formulation involves density exchange, e.g. in the case where the formulation alters on administration, e.g. from microparticles to a gel, so that the active ingredient diffuses or permeates out. Ion-based resins may also be used, the active component being released by ionic exchange, and wherein the rate of release can be controlled by using cationic or anionic forms of the drug. Another type of controlled-release formulation involves pulsed dosing. Further examples are given in U.S. Pat. No. 5,792,496.

An example of a controlled dose of active ingredient is dosing with a tablet containing 1.25 mg prednisolone. In this example, a patient taking a controlled dose of 1.25 mg prednisolone takes the tablet a number of hours before it is due to be released. Time zero on the plot (FIG. 1) denotes the earliest time at which active ingredient is released, probably midnight. The plasma levels achieved by release of the active agent at different times (2, 4 and 6 a.m.) are shown.

It can be seen that the range for $C_{max}$ obtained from the 1.25 mg prednisolone dose is from approximately 20 to 50 ng/ml (total prednisolone which includes protein bound and unbound active) depending on how quickly a patient absorbs the active ingredient. The time to $C_{max}$ or $T_{max}$ is usually between 1 and 3 hours. Where absorption is particularly fast, the $C_{max}$ may be 100 ng/ml total prednisolone or higher (this is not shown on the plot).

The following Study provides the basis of the present invention.

Study Design

The study was an assessor blind comparison of the effects of two doses of prednisolone (1 mg and 5 mg) given at 02.00. Patients stayed the night in hospital but were free to be up and about and to leave the hospital during the day. At 2 a.m. on the appropriate days patients were woken gently, administered the prednisolone, and settled back to sleep. Blood samples and clinical assessments were made at 08.30 and further clinical assessments related to symptoms on the day of drug administration at 12.00 and 08.30 the following day (except the final day when this last assessment was made before departure from the hospital). Patients were admitted on Monday and had a "control" night that evening with no prednisolone but full assessment the following day. On each of the following three nights prednisolone was administered. Patients went home on Friday afternoon but returned the following Monday to repeat the procedure. Allocation to 1 mg or 5 mg prednisolone in the first or second week was by randomization in sealed envelopes. The patient and assessor were not aware of which dose was given.

Outcome

Clinical: Outcome was measured at 08.30 each day for: swollen joint count (n=28); tender joint count (n=28); pain (0.100 mm, VAS). Outcome was measured at 12.00 each day for: morning stiffness (minutes); patient opinion of condition (0–100 mm, VAS); clinician opinion of condition (0–100 mm, VAS). Outcome was measured the following day for: whether the arthritis was worse in the morning or afternoon on the previous day (−1 morning, 0 equal, +1 afternoon).

Serological: Serum samples were obtained at 08.30, kept on ice for up to 1 hour, separated and stored at −70° C. to measure: C-reactive protein (CRP); IL-6 concentration; IL-6 soluble receptor (IL-6sR) concentration; hyaluronate (HA) concentration.

Procedure

Patients acted as their own control and took each dose of prednisolone for three consecutive nights. They were randomly allocated by cards kept in sealed envelopes to either 1 mg prednisolone on three consecutive nights followed by 5 mg on three consecutive nights, or the opposite sequence. The assessor was not aware of the treatment order allocation (and probably remained blind), but no placebo tablets were used and it was possible for a patient to be un-blind.

Patients invited to take part in the study had the following characteristics:

Over 18 years old

Had rheumatoid arthritis by the criteria of the American College of Rheumatology; see Arnett et al., Arthritis Rheum. 31:315–324 (1988)

Had active disease as evidenced by 3 or more swollen and tender joints

Were not taking glucocorticoid medication

Had not had intra-articular glucocorticoid injections in the previous 3 weeks

Had no medical conditions which, in the opinion of the investigator, would contraindicate low dose prednisolone therapy Informed consent was obtained and the patient prescription written by a doctor not associated with trial evaluation. Medication was dispensed at 2 a.m. on each treatment day after gently waking the patient. The patient was encouraged to settle back to sleep immediately.

On the morning before medication and on each morning on the day of medication, blood samples were taken at 8.30 a.m. and outcome assessments recorded then, and at noon, as indicated above.

Evaluation

Symptoms, signs and laboratory results were compared within and between patients, but the main assessment was visual inspection of the overall pattern of response. Means and standard deviations were used to define variation rates and for calculating trial size for future studies. An overall assessment of practicality and the potential for more frequent (but smaller volume) blood taking was made by discussion amongst the staff and patients involved.

Results

Three patients were able to take part in the study in the time available. One patient (3) was inadvertently given the first dose of treatment in the second week on the first night in hospital. Patient 3 took prednisolone for the next two nights and remained in hospital for a fourth night without prednisolone treatment. This patient's assessments have been included normally in the first week, but in the second week they have been used differently. Here, this patient's results have been included with those of the other patients in accordance with the dose of prednisolone received. This patient's final assessment (no prednisolone the night before) therefore appears as an extra day after the other patients in the study.

The results for 5 mg prednisolone place the patients in this pilot study well within the range of findings published by Arvidson et al. and reinforce the conclusions which can be drawn from that paper.

The results from 1 mg prednisolone raise the possibility that even at this dose there may be an appreciable effect on symptoms. Pain, EMS, patient's opinion and clinician's opinion were statistically significantly reduced, even with only three patients in the study. CRP and IL-6 were reduced significantly on 5 mg prednisolone and there was a tendency for reduction on 1 mg prednisolone.

All patents, patent applications, provisional applications, and publications referred to or cited herein are incorporated by reference in their entirety to the extent they are not inconsistent with the explicit teachings of this specification.

TABLE 1

Mean and 95% confidence intervals for each variable

| Day | Dose | Swollen Joints | Painful Joints | Pain | More or Less | EMS | Pt Opn | Cln Opn | CRP | HA | IL-6 | IL-6sR |
|---|---|---|---|---|---|---|---|---|---|---|---|---|
| | | | | | Mean Results | | | | | | | |
| 0 | 0 | 20.3 | 21.0 | 37.7 | −1.0 | 70.0 | 31.3 | 34.3 | 40.5 | 345.1 | 44.1 | 31557.8 |
| 1 | 1 | 18.7 | 20.0 | 26.0 | −0.7 | 55.0 | 23.7 | 28.7 | 35.5 | 241.9 | 28.1 | 31959.9 |
| 2 | 1 | 18.7 | 20.3 | 20.3 | −0.7 | 51.7 | 26.7 | 29.3 | 31.2 | 320.3 | 31.1 | 31468.0 |
| 3 | 1 | 18.3 | 20.3 | 16.7 | 0.0 | 40.0 | 12.7 | 16.3 | 25.8 | 372.5 | 22.8 | 30898.9 |
| 10 | 0 | 12.3 | 15.3 | 25.0 | −0.3 | 40.0 | 24.3 | 23.3 | 15.0 | 396.3 | 19.3 | 22937.2 |
| 11 | 5 | 18.0 | 19.0 | 19.7 | −0.3 | 30.0 | 19.3 | 27.7 | 36.6 | 322.5 | 30.3 | 42328.2 |
| 12 | 5 | 17.3 | 19.7 | 15.7 | −0.3 | 20.0 | 11.7 | 15.7 | 31.1 | 339.5 | 18.5 | 35331.6 |
| 13 | 5 | 14.0 | 19.7 | 16.0 | −0.7 | 33.3 | 13.3 | 11.7 | 19.1 | 193.9 | 13.8 | 36172.7 |
| 14 | 0 | 12.0 | 9.0 | 0.0 | 0.0 | 0.0 | 0.0 | 8.0 | 19.5 | 363.5 | 107.1 | 32180.5 |
| | | | | | 95% CI Results | | | | | | | |
| 0 | 0 | 0.7 | 5.7 | 24.9 | 0.0 | 19.6 | 20.3 | 14.1 | 17.1 | 213.0 | 18.1 | 8838.9 |
| 1 | 1 | 1.3 | 7.4 | 25.2 | 0.7 | 9.8 | 15.4 | 10.3 | 23.0 | 152.3 | 18.1 | 10225.5 |
| 2 | 1 | 3.5 | 7.7 | 20.3 | 0.7 | 8.6 | 5.7 | 10.5 | 27.5 | 321.8 | 32.7 | 10220.9 |
| 3 | 1 | 3.6 | 9.1 | 16.9 | 1.1 | 9.8 | 12.9 | 4.6 | 25.3 | 96.7 | 28.4 | 11329.4 |
| 10 | 0 | 15.2 | 19.2 | 31.8 | 0.8 | 48.0 | 30.2 | 29.6 | 22.8 | 718.7 | 23.3 | 27617.3 |
| 11 | 5 | 3.9 | 9.1 | 21.1 | 1.3 | 29.4 | 20.1 | 13.6 | 29.1 | 148.6 | 24.1 | 23485.3 |
| 12 | 5 | 6.5 | 9.6 | 15.4 | 0.7 | 19.6 | 11.6 | 1.7 | 26.0 | 221.4 | 23.6 | 8919.1 |
| 13 | 5 | 6.9 | 10.3 | 7.8 | 0.7 | 6.5 | 6.2 | 4.6 | 18.2 | 113.3 | 13.3 | 7069.5 |
| 14 | 0 | | | | | | | | | | | |

What is claimed is:

1. A unit dose formulation comprising less than 2.5 mg of prednisolone or an equivalent, equipotent amount of another corticosteroid.

2. The formulation according to claim 1, which comprises at least 0.25 mg of prednisolone or said equivalent.

3. The formulation according to claim 2, which comprises 0.5 to 2 mg of prednisolone or said equivalent.

4. The formulation according to claim 3, which comprises 1 to 1.25 mg of prednisolone or said equivalent.

5. The formulation according to claim 1, adapted to release at least 90% by weight of prednisolone or said equivalent 2 to 8 hours after administration.

6. The formulation according to claim 1, wherein said corticosteroid is a glucocorticoid.

7. The formulation according to claim 1, wherein said corticosteroid is selected from the group consisting of prednisone, budesonide, methylprednisolone, fluticasone, betamethasone, and deflazacort.

8. The formulation according to claim 7, wherein said corticosteroid is prednisone.

9. A method for the treatment of a patient suffering from a condition selected from the group consisting of asthma, inflammatory bowel disease, psoriasis, psoriatic arthritis, polymyalgia rheumatica, chronic obstructive pulmonary disease, and rheumatoid arthritis and other polyarthropathies, which comprises administering to the patient a unit dosage formulation comprising less than 2.5 mg of prednisolone or an equivalent, equipotent amount of another corticosteroid.

10. The method according to claim 9, wherein the formulation comprises at least 0.25 mg of prednisolone or said equivalent.

11. The method according to claim 10, wherein the formulation comprises 0.5 to 2 mg of the prednisolone or said equivalent.

12. The method according to claim 11, wherein the formulation comprises 1 to 1.25 mg of the prednisolone or said equivalent.

13. The method according to claim 9, wherein the formulation is adapted to release at least 90% by weight of the prednisolone or said equivalent 2 to 8 hours after administration.

14. The method according to claim 9, wherein said corticosteroid is a glucocorticoid.

15. The method according to claim 9, wherein said corticosteroid is selected from the group consisting of prednisone, budesonide, methylprednisolone, flutacasone, betamethasone, and deflazacort.

16. The method according to claim 15, wherein said corticosteroid is prednisone.

17. The method according to claim 8, wherein said corticosteroid is administered between midnight and 6 a.m.

* * * * *